United States Patent
Yen et al.

(10) Patent No.: US 7,935,535 B2
(45) Date of Patent: May 3, 2011

(54) NANOSTRUCTURE MATERIAL WITH METALLIC OXIDE AND METHOD FOR DETECTING PHOSPHORUS-CONTAINING COMPOUNDS

(75) Inventors: Shaw-Yi Yen, Hsinchu County (TW);
Shou-Nan Li, Nantou County (TW);
Bo-Jui Chen, Hsinchu County (TW);
Hong-Ping Lin, Taipei (TW)

(73) Assignee: Industrial Technology Research Institute, Hsinchu County (TW)

( * ) Notice: Subject to any disclaimer, the term of this patent is extended or adjusted under 35 U.S.C. 154(b) by 0 days.

(21) Appl. No.: 12/776,429

(22) Filed: May 10, 2010

(65) Prior Publication Data
US 2011/0065201 A1    Mar. 17, 2011

(30) Foreign Application Priority Data
Sep. 15, 2009   (TW) ............................... 98131018 A (51) Int. Cl.
*C30B 23/00*    (2006.01)
(52) U.S. Cl. ........................................ 436/104; 436/103
(58) Field of Classification Search .................. 436/104, 436/103
See application file for complete search history.

(56) References Cited

U.S. PATENT DOCUMENTS

| | | | |
|---|---|---|---|
| 5,250,260 A | 10/1993 | Nakano et al. | |
| 6,096,557 A | 8/2000 | Tanaka et al. | |
| 6,846,546 B2 * | 1/2005 | Kuroda et al. | 428/188 |
| 6,947,138 B2 | 9/2005 | Arno | |
| 2004/0034480 A1 * | 2/2004 | Binder | 702/24 |
| 2005/0048264 A1 * | 3/2005 | Miyata et al. | 428/166 |
| 2006/0147677 A1 * | 7/2006 | Miyata et al. | 428/166 |

FOREIGN PATENT DOCUMENTS

| | | |
|---|---|---|
| DE | 10159616 A1 | 6/2003 |
| GB | 2163553 A | 2/1986 |

OTHER PUBLICATIONS

Ozdemir S. et al., The potential of porous silicon gas sensor, 2007, Current Opinion in Solid State and Material Science, 11, 92-100.*

* cited by examiner

*Primary Examiner* — Walter D Griffin
*Assistant Examiner* — Christine T Mui
(74) *Attorney, Agent, or Firm* — Pai Patent & Trademark Law Firm; Chao-Chang David Pai (57) ABSTRACT

The invention provides a nanostructure material with metallic oxide including a product fabricated by the following steps: condensing silicon oxide or titanium oxide with a surfactant, obtaining a mesoporous silicon oxide or titanium oxide; mixing the mesoporous silicon oxide or titanium oxide with a metal or metallic compound and subjecting the mixture to a heterogeneous nucleation. According to another embodiment of the invention, the nanostructure material can also be fabricated by the following steps: subjecting silicon oxide or titanium oxide and a carbon black template to a calcination; mixing the results with a metal or metallic compound; and subjecting the mixture to a second calcinations. Further, in the invention, a method for detecting phosphorus-containing compounds employing the aforementioned nanostructure material is also provided.

23 Claims, 11 Drawing Sheets

ND METHOD FOR
NANOSTRUCTURE MATERIAL WITH METALLIC OXIDE AND METHOD FOR DETECTING PHOSPHORUS-CONTAINING COMPOUNDS

CROSS REFERENCE TO RELATED APPLICATIONS

This application is based upon and claims the benefit of priority from the prior Taiwan Patent Application No. 098131018, filed on Sep. 15, 2009, the entire contents of which are incorporated herein by reference.

BACKGROUND OF THE INVENTION

1. Field of the Invention

The present invention relates to a nanostructure material, and in particular relates to a nanostructure material with metallic oxide serving as detecting material for a gas detector.

2. Description of the Related Art

Monitoring and controlling micro contaminants, is one of the most important issues for IC manufactures, as critical dimensions continue to shrink.

International Technology Roadmap for Semiconductor (ITRS) predicts that the critical dimensions of a chip scale will shrink to 32 nm in 2013. Thus, controlling micro contaminants is critical for IC manufacturers. For example, for 32 nm semiconductor processes, a recommended sensitive area micro contaminants (such as acid, base, organic compounds or dopants) value for a clean room is less than 10 ppt to 150 ppt. Therefore, a gas sensor having a low detection limit is needed, to assure that the air quality in a clean room meets advanced semiconductor process requirements.

Commonly used gases and its by-products during the IC fabrication process can be classified into: flammable gas, such as silicon methane, methane or the likes; toxic gas, such as arsine, diborane, phosphine or the likes; corrosive gas, such as hydrogen fluoride, hydrogen chloride or the likes; and greenhouse gas, such as tetrafluoromethane, nitrogen trifluoride or the likes, depending on their chemical properties and influences. These toxic, hazardous gases may be produced during a thin film, chemical vapor deposition, dry etching, diffusion, ion implantation and epitaxy process.

Phosphine is a colorless gas, when in a room temperature environment. It has a nauseating garlic smell and is toxic. Breathing in phosphine by humans, can cause difficulty in breathing, which may lead to death. Furthermore, phosphine is also dangerous because it is a flammable gas having explosion limits between 1.6% and 98%. However, phosphine is often used as an N-type dopant which is doped into polysilicon by diffusion or ion implantation. Therefore, phosphine gas sensors must be installed in semiconductor foundries in accordance with legal requirements At present, commercial phosphine gas sensors are mainly classified into electrochemical detectors and ribbon detectors, which dominate over 90% of the phosphine gas sensor market. The detection limit of commercial phosphine gas sensors is about 100 ppb in accordance with law, which is 1,000-10,000 times greater than the recommended value by the ITRS. Meanwhile, it is easy for other gases to interfere with the commercial phosphine gas sensors. Thus, in order to address the above problems, the current detection methods that foundries use is traditional sampling and analysis. The method includes exposing chips to the clean room atmosphere for 24-48 hours, bringing the contaminants deposited on the chip surface to an acidic solution by concentrated HF acid, and analyzing the contaminants by using inductively coupled plasma mass spectrometry (ICP-MASS). However, a lot of time, labor and materials are required for the method, and real-time detection is not accomplished; thereby lowering fabrication yields.

Other phosphorus-containing molecules, such as a phosphorusic acid, are corrosive for the eyes, skin, and respiratory tract of humans, and may cause blindness and permanent injuries. Phosphorusic acid may decompose to toxic phosphorus oxides. Therefore, phosphorusic acid is hazardous for humans.

Accordingly, a novel material and technique for detecting phosphorus-containing compounds is desired to address the described problems.

BRIEF SUMMARY OF THE INVENTION

An exemplary embodiment of a nanostructure material with metallic oxide includes a product fabricated by the following steps: mixing a silicon oxide or titanium oxide with a surfactant to obtain a first mixture, and subjecting the first mixture to a condensation reaction at a first pH value to obtain a mesoporous silicon oxide or titanium oxide; mixing a metal or metallic compound and the mesoporous silicon oxide or titanium oxide to obtain a second mixture, and adjusting the second mixture to a second pH value; and subjecting the second mixture to a heterogeneous nucleation, preparing a silicon oxide or titanium oxide nanostructure material with metallic oxide located on a surface thereof.

Further, in another exemplary embodiment of the invention, the nanostructure material with metallic oxide can include a product fabricated by the following steps: subjecting a first mixture, including a silicon-containing or titanium-containing compound and a carbon template, to a first annealing process to obtain a powder; mixing a metal or metallic compound with the powder to obtain a second mixture; and subjecting the second mixture to a second annealing process, and preparing a silicon oxide or titanium oxide nanostructure material with metallic oxide located on a surface thereof, wherein, for the nanostructure material with metallic oxide, the weight ratio between the silicon or titanium and metal of the metallic oxide is between 0.99:0.01 to 0.5:0.5.

The invention further provides a method for detecting phosphorus-containing compounds, including the following steps: providing a nanostructure material with metallic oxide; introducing a gas sample to react with the nanostructure material with metallic oxide; and analyzing results of the reaction.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a nanostructure material with metallic oxide. The nanostructure material with metallic oxide is highly selective to phosphorus-containing compounds, and can be used to serve as material for detecting phosphorus-containing compounds.

In an embodiment, the nanostructure material with metallic oxide can be prepared by the following steps. A silicon oxide or titanium oxide is mixed with a surfactant at a first pH value to obtain a mesoporous silicon oxide or titanium oxide. Before mixing the silicon oxide or titanium oxide with the surfactant, a base can be mixed with the silicon oxide or titanium oxide and heated. Next, a metal or metallic compound is mixed with the mesoporous silicon oxide or titanium oxide mixture to obtain a mixture, and the mixture can be modified to a second pH value. Next, the mixture is subjected to heterogeneous nucleation to prepare a silicon oxide or titanium oxide nanostructure material with metallic oxide located on a surface thereof.

Herein, silicon oxide or titanium oxide may be silicon oxide particles, aluminum oxide particles or titanium oxide particles, such as P-25, MCM-41, or SBA-15. The inorganic oxide particles have a surface area of about 50 $m^2$/g to 1200 $m^2$/g. The surfactant can be gelatine, or quaternary ammonium salts. The metal includes Cu, Ag, Cr, Au, Pt, Pd, or combinations thereof. Further, the metallic compound includes halide of Cu, Ag, Cr, Au, Pt, or Pd, nitrate of Cu, Ag, Cr, Au, Pt, or Pd, phosphate of Cu, Ag, Cr, Au, Pt, or Pd, sulfate of Cu, Ag, Cr, Au, Pt, or Pd, or combinations thereof. In the nanostructure material with metallic oxide, the weight ratio between the silicon or titanium and metal of the metallic oxide is between 0.99:0.01 to 0.5:0.5. Namely, the weight percentage of the metal of the metallic oxide can be between 1-50 wt %, based on the whole weight of the silicon or titanium and metal of the metallic oxide. When the weight percentage of the metal of the metallic oxide is more than 50 wt %, the metallic oxide is apt to aggregate and have a large grain size; thereby reducing the active region surface area and reaction activity. On the other hand, when the weight percentage of the metal of the metallic oxide is less than 1 wt %, the metallic oxide has a relatively low active region surface area, resulting in reduced reaction activity.

The reaction conditions of the nanostructure material with metallic oxide are disclosed as below. The first pH value can be less than 5 (such as 5 or 3), the second pH value can be between 6-11 (such as 7), and the temperature of the heterogeneous nucleation can be between 80-140° C. The term "heterogeneous nucleation" refers to nucleation that was initiated by foreign particles (also called nucleation sites) in the solution.

An acid can be added to adjust the pH value of the solution. In one embodiment, the acid includes hydrochloric acid, sulfuric acid, phosphorusic acid, nitric acid or combinations thereof. For instance, when the added metal salt is copper (II) chloride or aluminum (III) chloride, hydrochloric acid is preferably used to adjust the pH value of the solution. The pH value of the solution is between about 1.0 and about 3.0 for hydrolyzing the monomer of the sol-gel inorganic oxides. A base can also be added to adjust the pH value of the solution. In one embodiment, the base may be an aqueous solution of a commonly used inorganic alkaline salt, such as sodium hydroxide, potassium hydroxide, sodium carbonate or sodium bicarbonate.

After heterogeneous nucleation, the silicon oxide or titanium oxide nanostructure material with metallic oxide located on a surface thereof can be further subjected to an annealing process, wherein the annealing process has an annealing temperature of more than 300° C.

In another embodiment of the invention, the nanostructure material with metallic oxide can include a product fabricated by the following steps. A silicon-containing or titanium-containing compound can be mixed with a carbon template and then subjected to a first annealing process, obtaining a powder. Next, the powder is further mixed with a metal or metallic compound to obtain a mixture. Finally, the mixture is subjected to a second annealing process, preparing a silicon oxide or titanium oxide nanostructure material with metallic oxide located on a surface thereof. In the nanostructure material with metallic oxide, the weight ratio between the silicon or titanium and metal of the metallic oxide is between 0.99:0.01 to 0.5:0.5. Namely, the weight percentage of the metal of the metallic oxide can be between 1-50 wt %, based on the whole weight of the silicon or titanium and metal of the metallic oxide. When the weight percentage of the metal of the metallic oxide is more than 50 wt %, the metallic oxide is apt to aggregate and have a large grain size; thereby reducing the active region surface area and reaction activity. On the other hand, when the weight percentage of the metal of the metallic oxide is less than 1 wt %, the metallic oxide has a relatively low active region surface area, resulting in reduced reaction activity.

The silicon-containing or titanium-containing compound has a chemical structure represented by $M(OR)_4$, wherein M is silicon or titanium, and R is $C_{1-8}$ alkyl group. The silicon-containing or titanium-containing compound can be titanium (IV) isopropoxide (TTIP), 3-aminopropyltriethoxysilane (APTES), tetraethoxysilane (TEOS) or combinations thereof. Further, the first annealing process can have an annealing temperature of more than 500° C., and the second annealing process can have an annealing temperature of more than 300° C.

Before the steps of mixing or condensing, a solvent can be added. In embodiments of the invention, the solvent includes, but is not limited to, water, methanol, ethanol, propanol, isopropanol, acetone or combinations thereof.

According to embodiments of the invention, a method for detecting phosphorus-containing compounds is provided, and the method includes the following steps: providing the aforementioned nanostructure material, introducing a gas sample (including phosphorus-containing compound) to react with the nanostructure material; and analyzing results of the reaction. The phosphorus-containing compounds include phosphine, phosphorusic acid, dimethyl methylphosphonate, trimethyl phosphite, trimethyl phosphate, parathion, parathion methyl, or combinations thereof. In comparison with a conventional method for detecting phosphorus-containing compounds, the method of the invention employs nanostructure materials having high selectivity for phosphorus-containing compounds. The nanostructure materials may be further used as a sensor for a phosphorus-containing compound detector. The sensor would have a detection limit of between about 300 ppm and about 100 ppb.

In one further embodiment, the sensor may be connected to a Fourier transform infrared spectrum (FT-IR) system to form a real-time phosphorus gas detector. A gas sample and a carrier gas such as nitrogen or noble gases would respectively pass through different mass flow controllers and mixed together. The mixed gas is introduced to the sensor which is formed by the nanostructure materials, wherein the sensor is connected to an FT-IR system. Accordingly, sensor variations would be detected by the FT-IR system and the results would be transferred to a data processing and storage device 116 in real-time.

The following examples are intended to illustrate the invention more fully without limiting their scope, since numerous modifications and variations will be apparent to those skilled in this art.

Example 1

Figure 1:
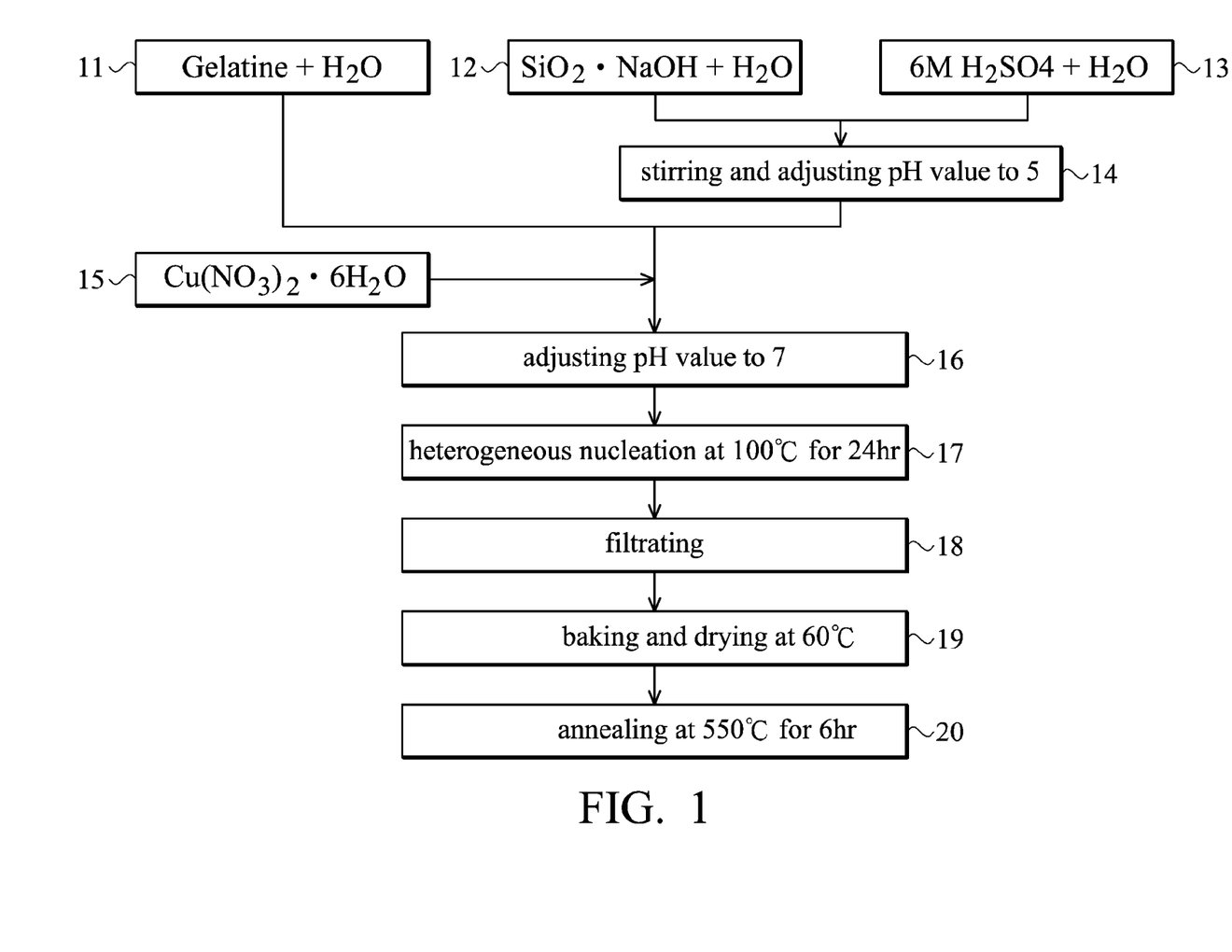
FIG. 1 shows a flow chart of a method for fabricating the nanostructure material with metallic oxide according to Example 1.

FIG. 1 shows a flow chart of a method for fabricating the nanostructure material with metallic oxide according to an embodiment of the invention. First, 2.0 g of gelatine was dissolved in 20 g of H2O, obtaining a solution 1 (step 11). Next, 8 g of SiO2.NaOH was dissolved in 50 g of $H_2O$, obtaining a solution 2 after mixing (step 12). Next, 5 g of $H_2SO_4$ (6M) was dissolved in 100 g of $H_2O$, obtaining a solution 3 (step 13). Next, the solution 2 and solution 3 were mixed and the pH value was adjusted to 5.0. After stirring for 3 min, a solution 4 was obtained (step 14).

Next, the solution 1 and solution 4 were mixed. After stirring for 10 min, a solution 5 was obtained. Next, the pH value of the solution 5 was adjusted by adding a solution of $Cu(NO_3)_2 \cdot 6H2O$ dissolved in $H_2O$, obtaining a solution 6 with a pH value of 7 (steps 15 and 16).

After filtration of the solution 6, the precipitate was washed with DI water and dried in an oven. After performing heterogeneous nucleation at 100° C. for 24 hrs (step 17) and filtrating (step 18), the precipitate was dried in an oven at 60° C. (step 19). After drying, the result was put into a furnace and subjected to an annealing process at 550° C. for 6 hrs (step 20), obtaining a nanostructure material with Cu oxide.

Figure 2:
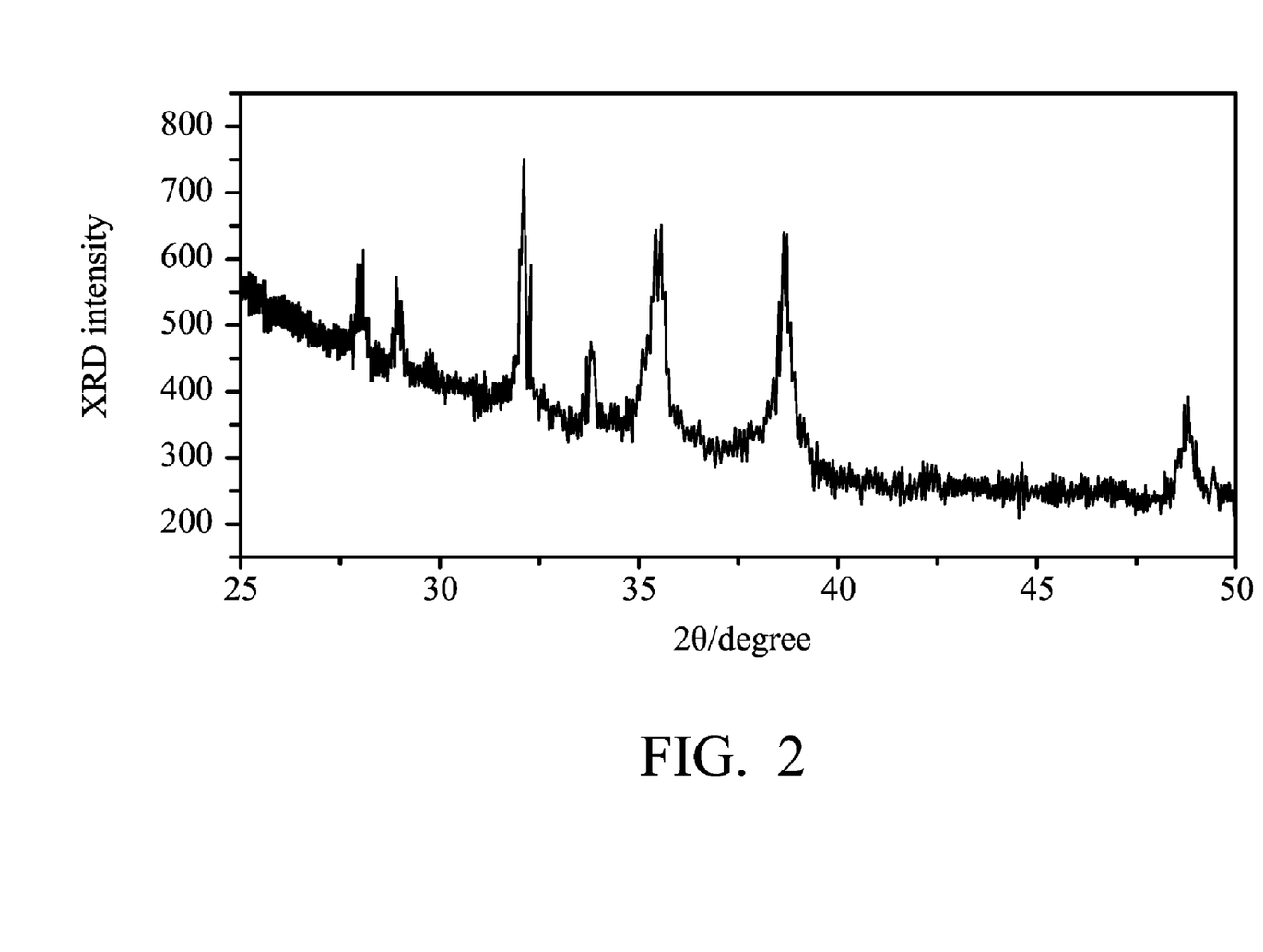
FIG. 2 shows an X-ray diffraction (XRD) plot of the nanostructure material of Example 1.

FIG. 2 shows an X-ray diffraction (XRD) plot of the nanostructure material with Cu oxide. The nanostructure material has a mesoporous structure with well-distributed Cu atoms. Next, the surface of the nanostructure material was analyzed by an energy dispersive X-ray (EDX) spectrometer. The results of the measurements show that the ratio between the copper and the silicon of the nanostructure material was 28:72. Finally, the surface area and pore size distribution of the nanostructure material were measured by the BET (Brunauer, Emmett and Teller) method, and the nanostructure material has a surface area of 780 $m^2/g$ and a pore size distribution of 2.5 nm.

Examples 2-13

Similar processes to that according to Example 1 were performed for Examples 2-13 except that $Cu(NO_3)_2 \cdot 6H_2O$ was replaced with various metallic compounds. The employed metallic compounds and the obtained nanostructure materials of Examples 2-13 are shown in Table 1.

TABLE 1

| Example No. | metallic compound | product |
|---|---|---|
| 2 | $AgNO_3$ | nanostructure material with Ag oxide |
| 3 | $Cr(NO_3)_3 \cdot 9H_2O$ | nanostructure material with Cr oxide |
| 4 | $HAuCl_4 \cdot 3H_2O$ | nanostructure material with Au oxide |
| 5 | $H_2PtCl_6 \cdot xH_2O$ | nanostructure material with Pt oxide |
| 6 | $PdCl_2$ | nanostructure material with Pd oxide |
| 7 | $Co(NO_3)_2 \cdot 6H_2O$ | nanostructure material with Co oxide |
| 8 | $Al(NO_3)_3 \cdot 9H_2O$ | nanostructure material with Al oxide |
| 9 | $Mn(NO_3)_2 \cdot 4H_2O$ | nanostructure material with Mn oxide |
| 10 | $Ni(NO_3)_2 \cdot 6H_2O$ | nanostructure material with Ni oxide |
| 11 | $Fe(NO_3)_3 \cdot 9H_2O$ | nanostructure material with Fe oxide |
| 12 | $Ce(NO_3)_3 \cdot 6H_2O$ | nanostructure material with Ce oxide |

Figure 3:
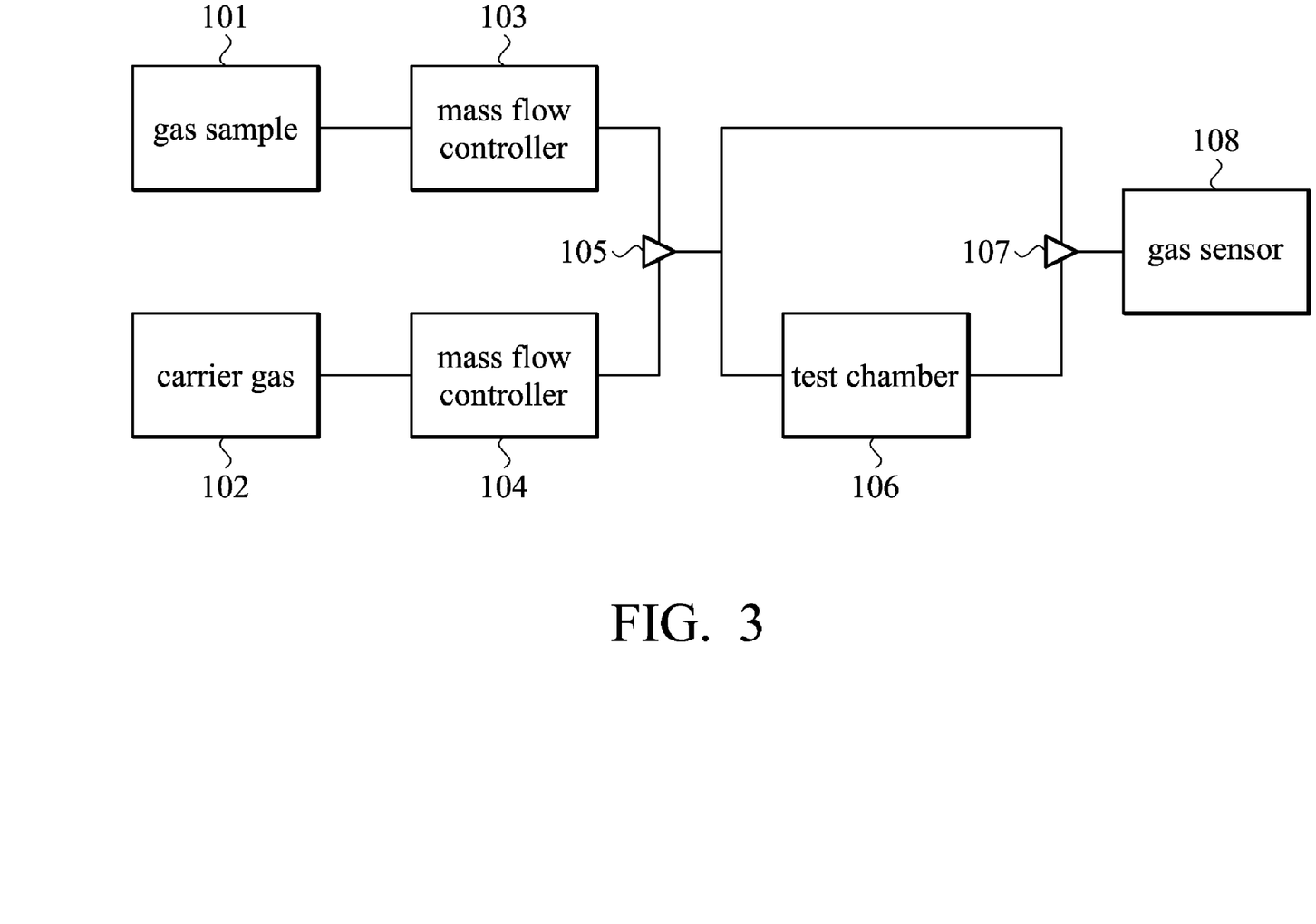
FIG. 3 is a schematic view illustrating a detector for detecting phosphorus-containing compounds according to an embodiment of the invention.

0.1 g of nanostructure materials of Examples 1-13 were respectively disposed in a test chamber 106 of the device shown in FIG. 3 and the absorption efficiency for $PH_3$ of the nanostructure materials was measured. A gas sample ($PH_3$ with a concentration of 500 ppb) 101 and a carrier gas 102 such as nitrogen or noble gases were respectively passed through different mass flow controllers 103, and 104 and mixed together. Valves 105 and 107 were used to control the mixed gas introduced to the test chamber 106 with the nanostructure material therein or introduced to the gas sensor 108 directly for measuring the content of $PH_3$. The nanostructure material was disposed in the test chamber 106 and a carrier platform of the test chamber 106 was covered with the nanostructure material. When the mixed gas was introduced into the chamber, the mixed gas was forced to completely pass thorough the nanostructure material. After adsorption, the remaining gas was measured by the gas sensor 108.

Figure 4:
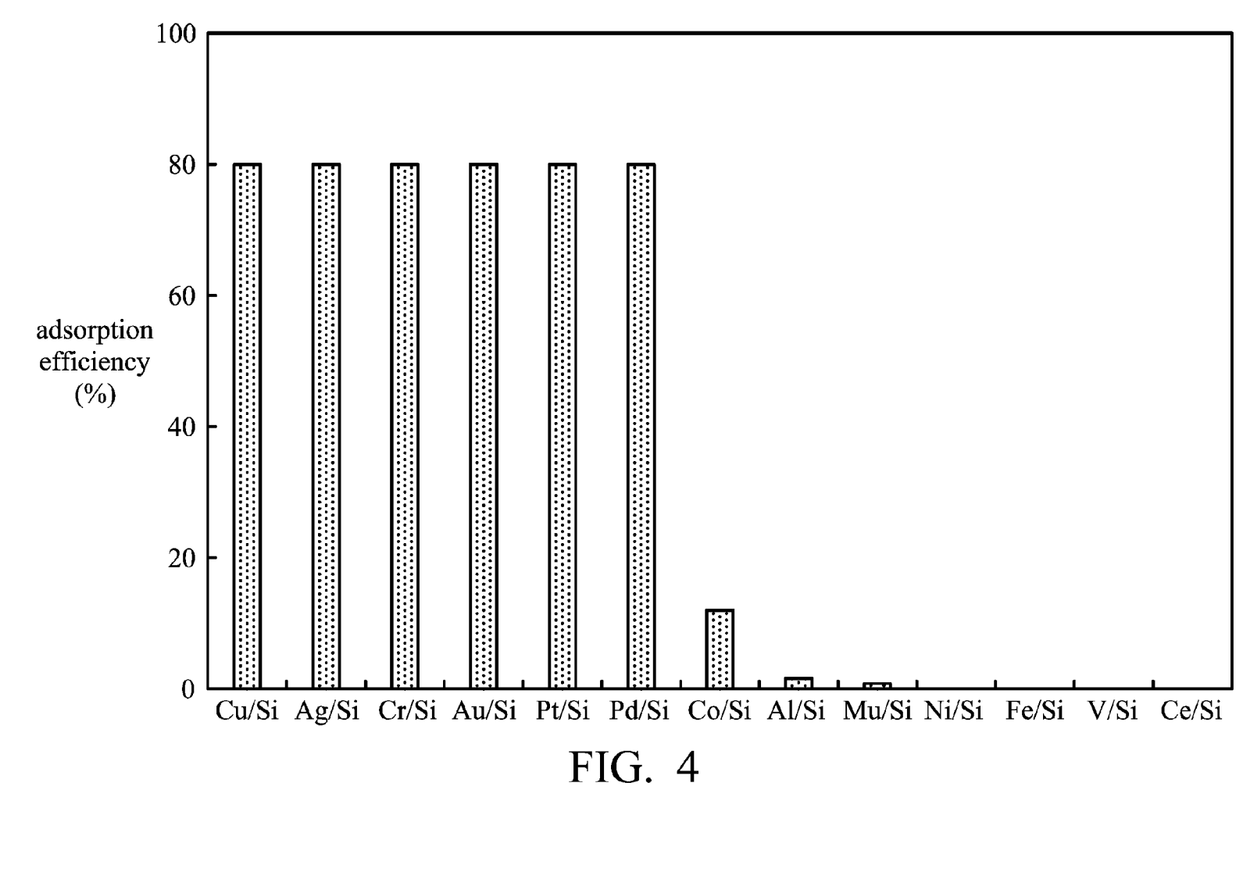
FIG. 4 shows a graph plotting the absorption efficiency of the nanostructure materials of Examples 1-13.

The adsorption efficiency of the nanostructure materials of Example 1-13 were measured and the results are shown in FIG. 4. Accordingly, the nanostructure materials with Cu, Cr, Ag, Au, Pt, or Pb oxide had high adsorption efficiency, exceeding the detection limit of 80%.

Example 14

Figure 5:
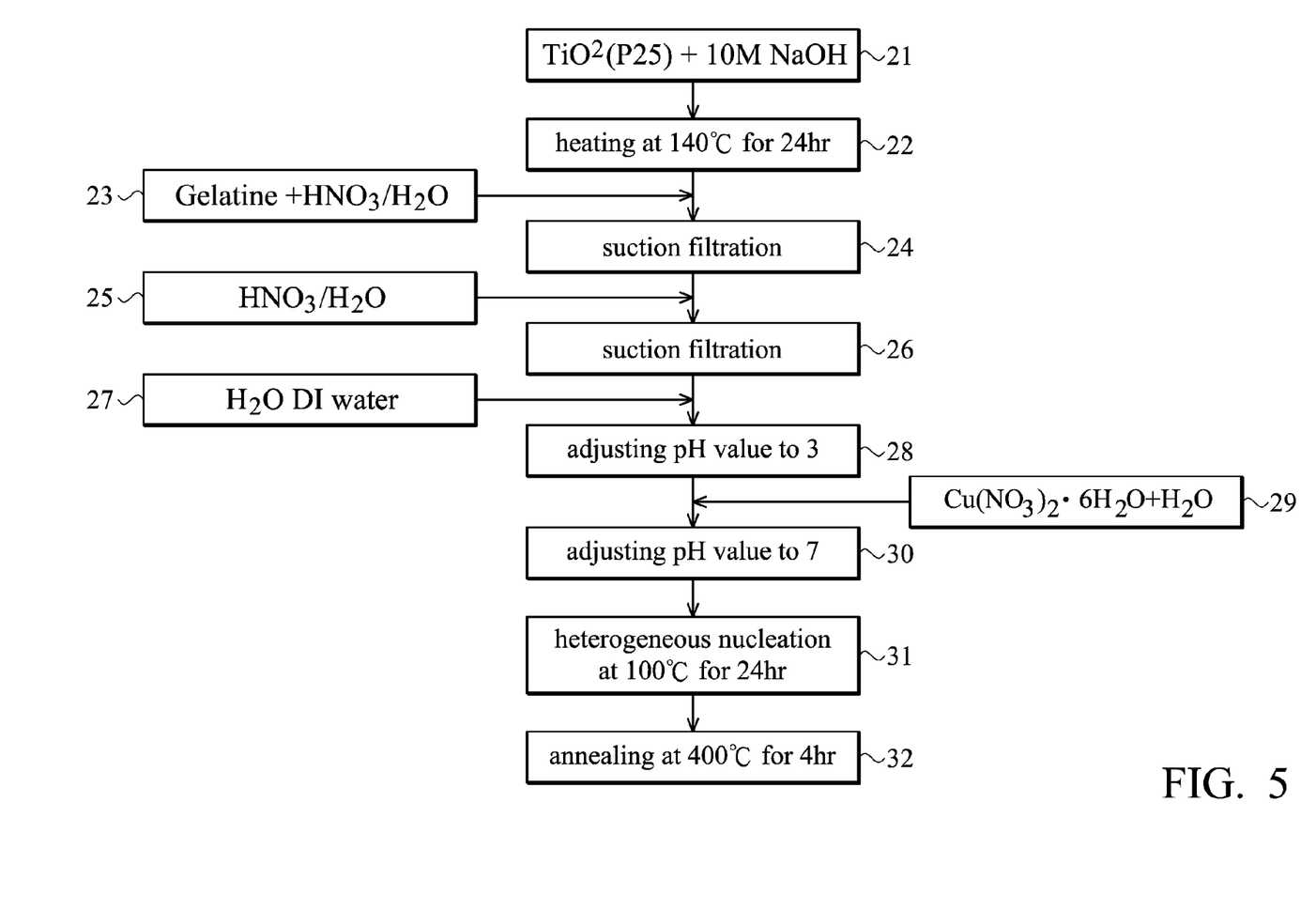
FIG. 5 shows a flow chart of a method for fabricating the nanostructure material with metallic oxide according to Example 14.
Figure 6:
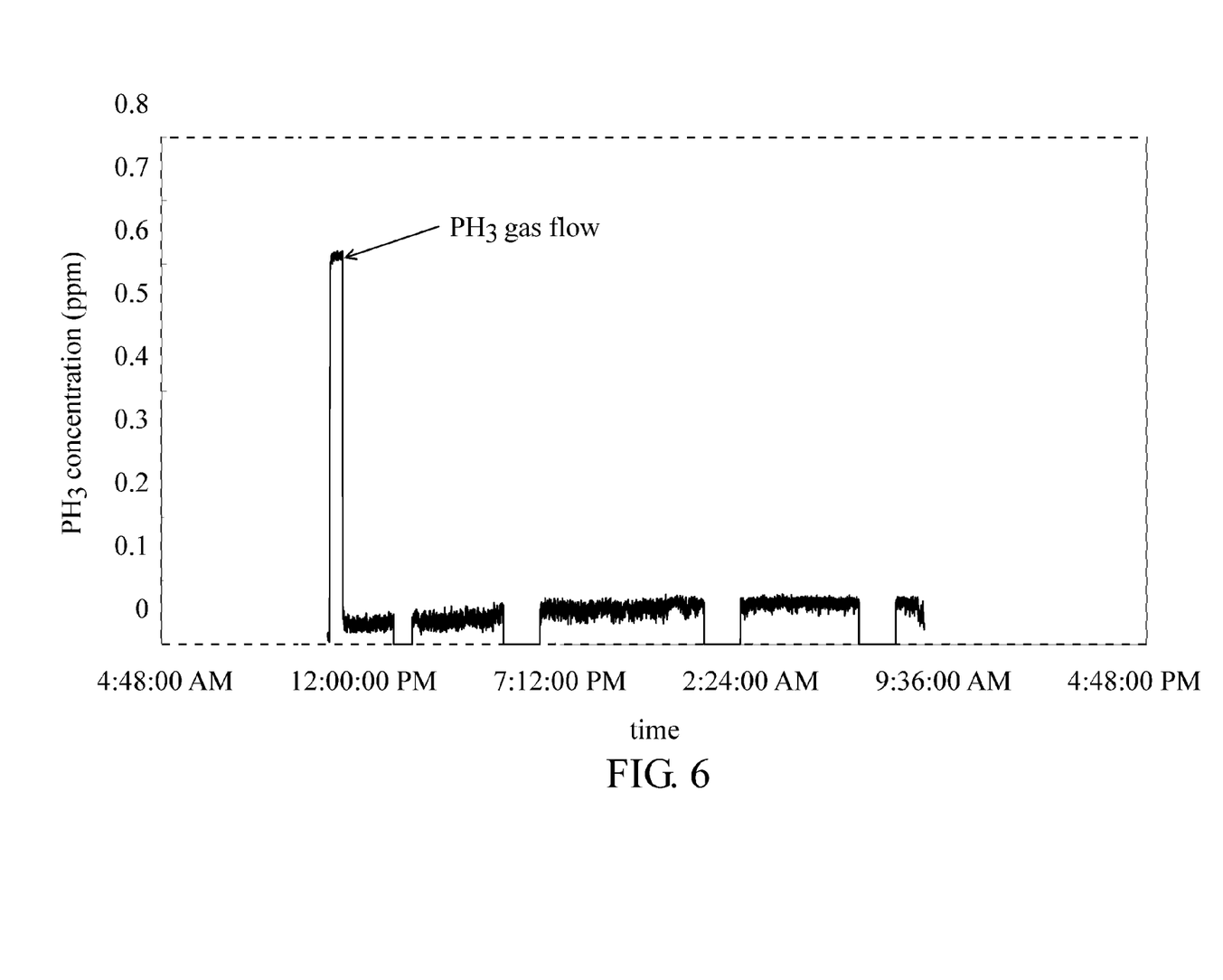
FIG. 6 shows a graph plotting absorption efficiency against time of the nanostructure material of Example 14.

FIG. 5 shows a flow chart of a method for fabricating the nanostructure material with metallic oxide according to an embodiment of the invention. First, 0.625 g of $TiO_2$ (P25) was mixed with 12.5 ml of NaOH (10M), and then the mixture was stirred for 1 hr (step 21). After heating at 140° C. for 24 hrs by an autoclave (step 22), a solution 1 was obtained. Next, 1.875 g of gelatine was dissolved in 1.3 ml of $HNO_3/200$ ml of $H_2O$, obtaining a solution 2 (step 23). Next, the solution 2 was added into the solution 1, and then the mixture was stirred at 40° C. for 24 hrs. After acid washing, the precipitate was subjected to suction filtration (step 24), and the result was mixed with 1.3 ml of $HNO_3/200$ ml of $H_2O$ and stirred at 40° C. (step 25). After suction filtration (step 26), the result was dissolved in 50 g of DI water (step 27) and then the pH value of the result was adjusted, obtaining a solution 3 with a pH value of 3 (step 28). Next, 0.625 g of copper nitrate was dissolved in 20 g of DI water, obtaining a solution 4 (step 29). Next, the solution 4 was added into the solution 3 (step 30). After stirring for 5 min, the pH value of the result was adjusted to 7 (step 31). Next, the result was put in an oven and subjected to a hydrothermal treatment at 100° C. for 1 day to perform heterogeneous nucleation. Finally, after drying, the result was heated to 400° C. for 4 hrs by a furnace, and then subjected to an annealing process at 400° C. for 4 hrs, obtaining titanium oxide nanostructure materials with Cu oxide (step 32). The adsorption efficiency of the nanostructure materials of Example 14 was measured and the result is shown in FIG. 6. Accordingly, the nanostructure materials with Cu oxide had high adsorption efficiency, exceeding the detection limit of 83%.

Example 15

Figure 7:
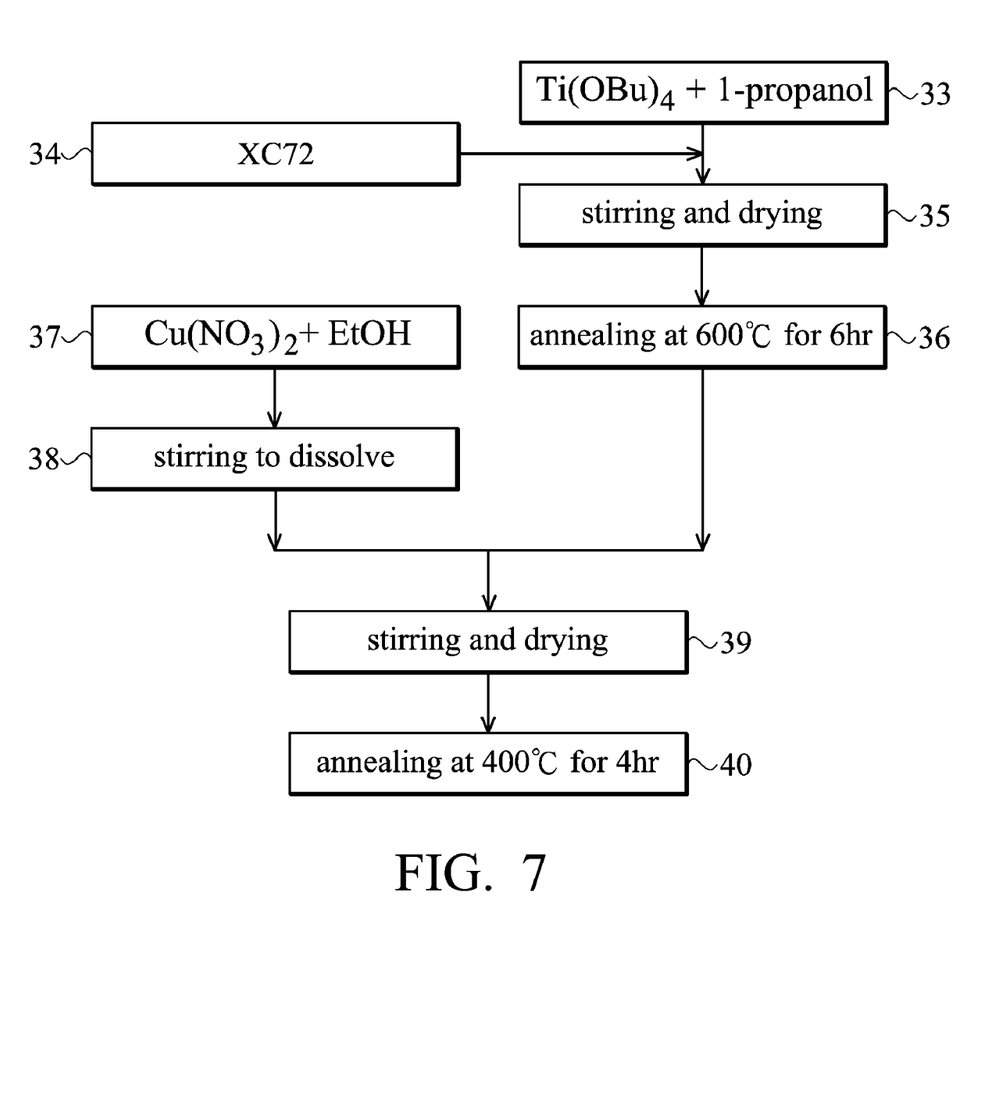
FIG. 7 shows a flow chart of a method for fabricating the nanostructure material with metallic oxide according to Example 15.

FIG. 7 shows a flow chart of a method for fabricating the nanostructure material with metallic oxide according to another embodiment of the invention. First, 1.5 g of Ti(OBu)$_4$ was mixed with 15 ml of 1-propanol, and then the mixture was stirred (step 33).

Next, 1.5 g of XC72 (carbon template) was added into the solution 1 (step 34). After stirring and drying (step 35), the result was subjected to an annealing process at 600° C. for 6 hrs (step 36), obtaining a powder 1. Next, 1.017 g of Cu(NO$_3$)$_2$ was dissolved in 20g of EtOH (step 37) and stirred (step 38), obtaining a solution 2. Next, the powder 1 was added into the solution 2. After stirring and drying (step 39), the result was subjected to an annealing process at 400° C. for 4 hrs (step 40), obtaining a titanium oxide nanostructure material with Cu oxide.

Figure 8:
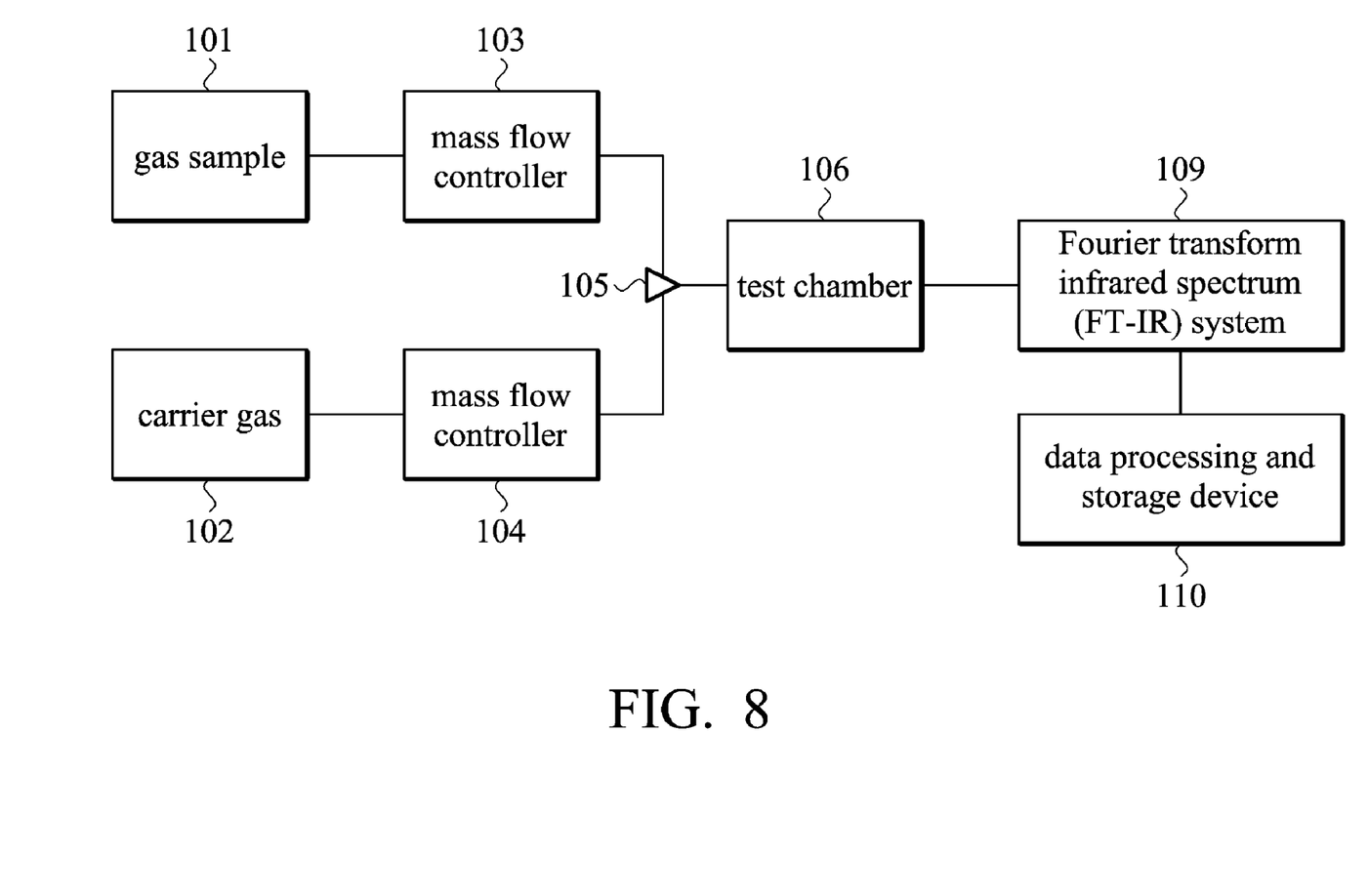
FIG. 8 is a schematic view illustrating a gas detector connected to an FT-IR system according an embodiment of the invention.

0.05 g of the obtained nanostructure material was put into a test chamber 106 connected to a Fourier transform infrared spectrum (FT-IR) system 109, as shown in FIG. 8. A gas sample 101 and a carrier gas 102 were introduced from the top of the test chamber 106, passing through a platform covered with the nanostructure material. The FT-IR spectrum of the nanostructure material was recorded every 2 min during the introduction of the gas sample and the carrier gas.

Nanostructure material variations can be detected by the FT-IR system 109 and the results can be transferred to a data processing and storage device 110 in real-time. The adsorbed PH$_3$ gas is transformed to a phosphorus-containing oxide via reaction with the nanostructure material, and the phosphorus-containing oxide has absorption peaks at about 996 cm$^{-1}$, 1081 cm$^{-1}$, and 1131 cm$^{-1}$, showing P—O bonding of the phosphorus-containing oxide.

Figure 9:
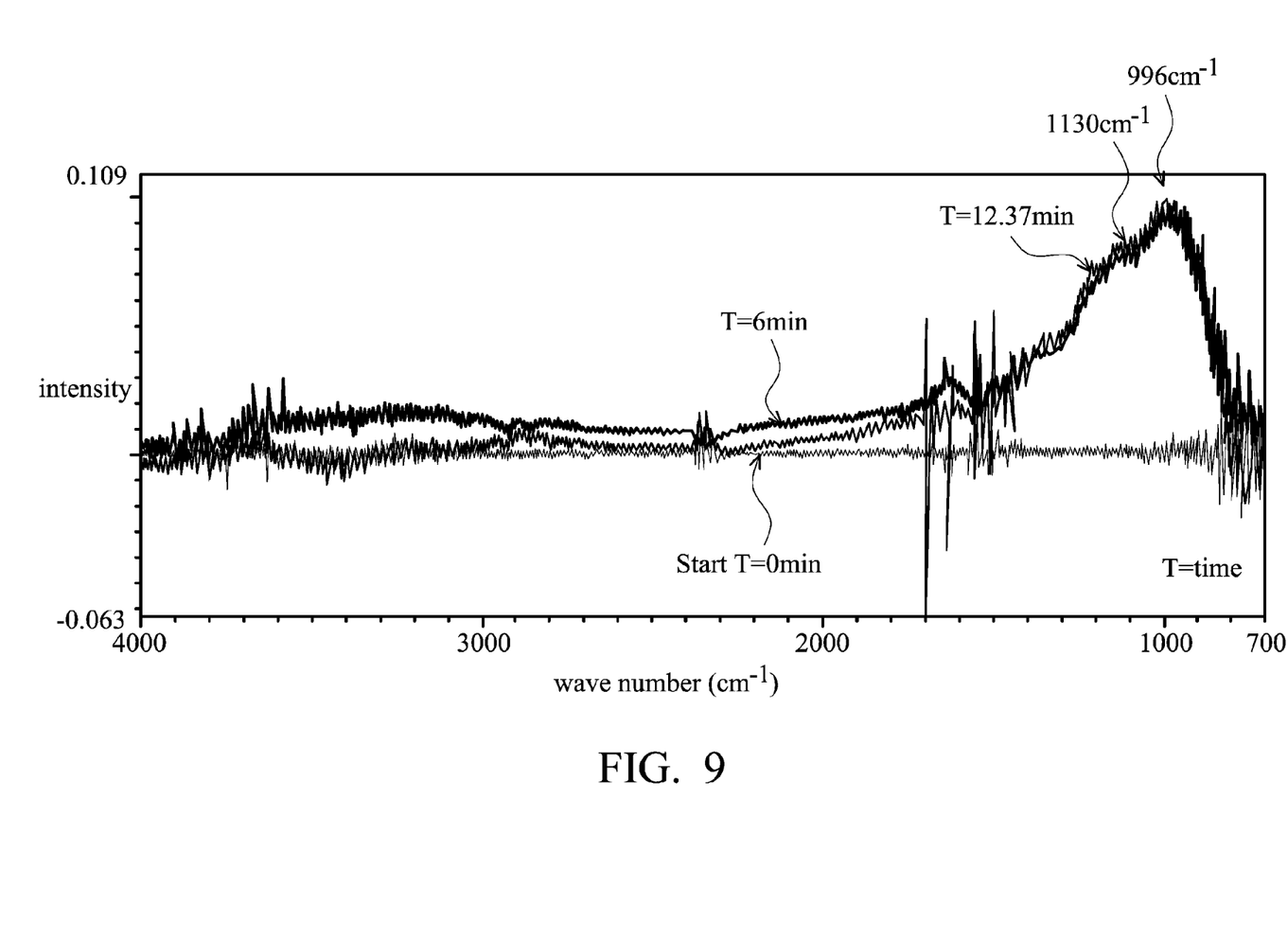
FIG. 9 is an FT-IR spectrum of the nanostructure material of Example 15 after adsorbing $PH_3$.
Figure 10:
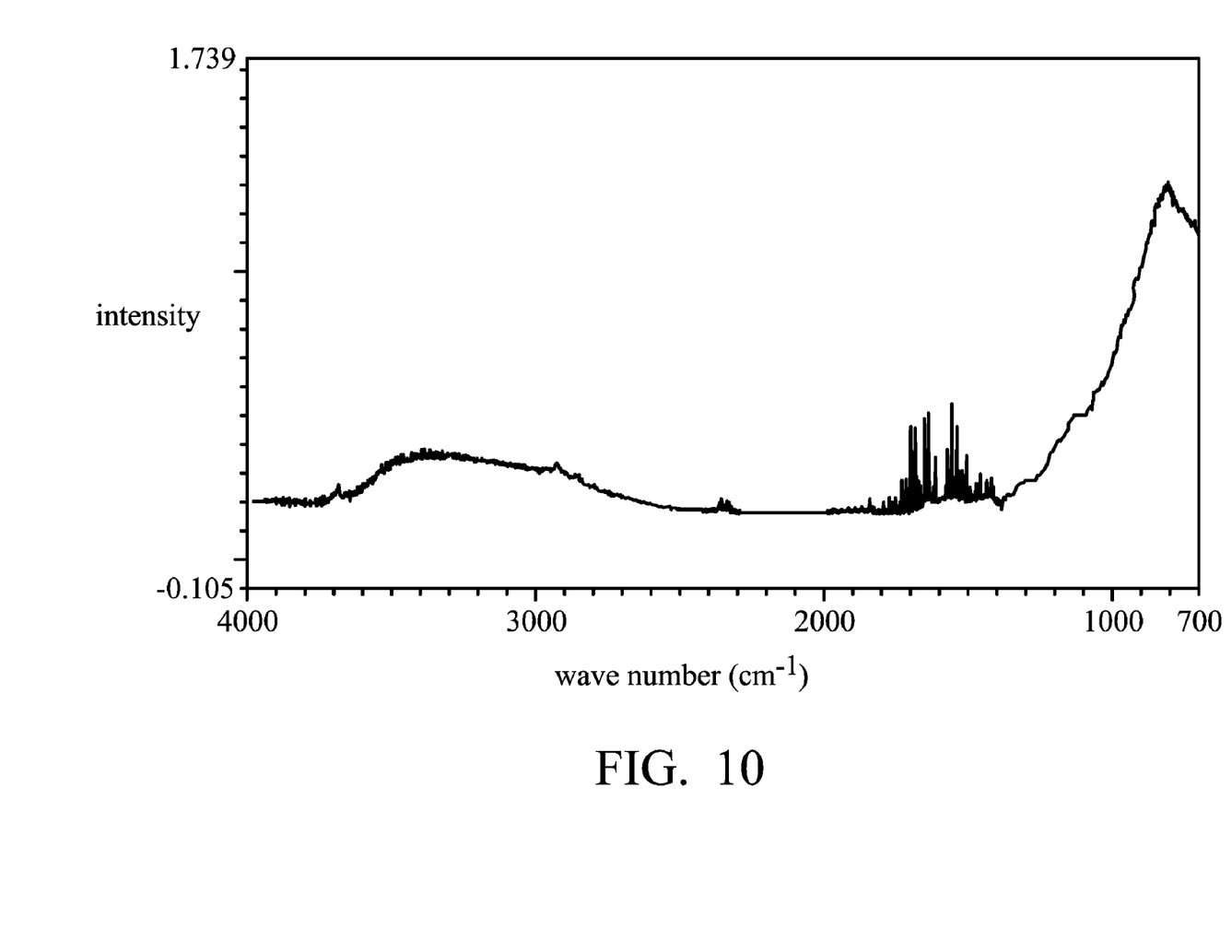
FIG. 10 is an FT-IR spectrum of the nanostructure material of Example 15.

The FT-IR spectrum of Example 15 is shown in FIG. 9. The PH$_3$ concentration of the gas sample was 500 ppb and the gas flow or the gas sample was 200 cc/min. The absorption peaks of the absorption peak were immediately shown in the FT-IR spectrum within two minutes. Therefore, the nanostructure material of the invention can serve as detecting material for detecting PH$_3$. Further, the nanostructure material can be connected to an FT-IR system to form a real-time gas detector.

Examples 16-20

For Examples 16-20, similar processes with that according to Example 15 were performed, except that Cu(NO$_3$)$_2$ · 6H$_2$O was replaced with various metallic compounds. The employed metallic compounds and obtained nanostructure materials of Examples 16-20 are shown in Table 2.

TABLE 2

| Example No. | metallic compound | Product |
|---|---|---|
| 16 | AgNO$_3$ | nanostructure material with Ag oxide |
| 17 | Cr(NO$_3$)$_3$·9H$_2$O | nanostructure material with Cr oxide |
| 18 | HAuCl$_4$·3H$_2$O | nanostructure material with Au oxide |
| 19 | H$_2$PtCl$_6$·xH$_2$O | nanostructure material with Pt oxide |
| 20 | PdCl$_2$ | nanostructure material with Pd oxide |

Figure 11:
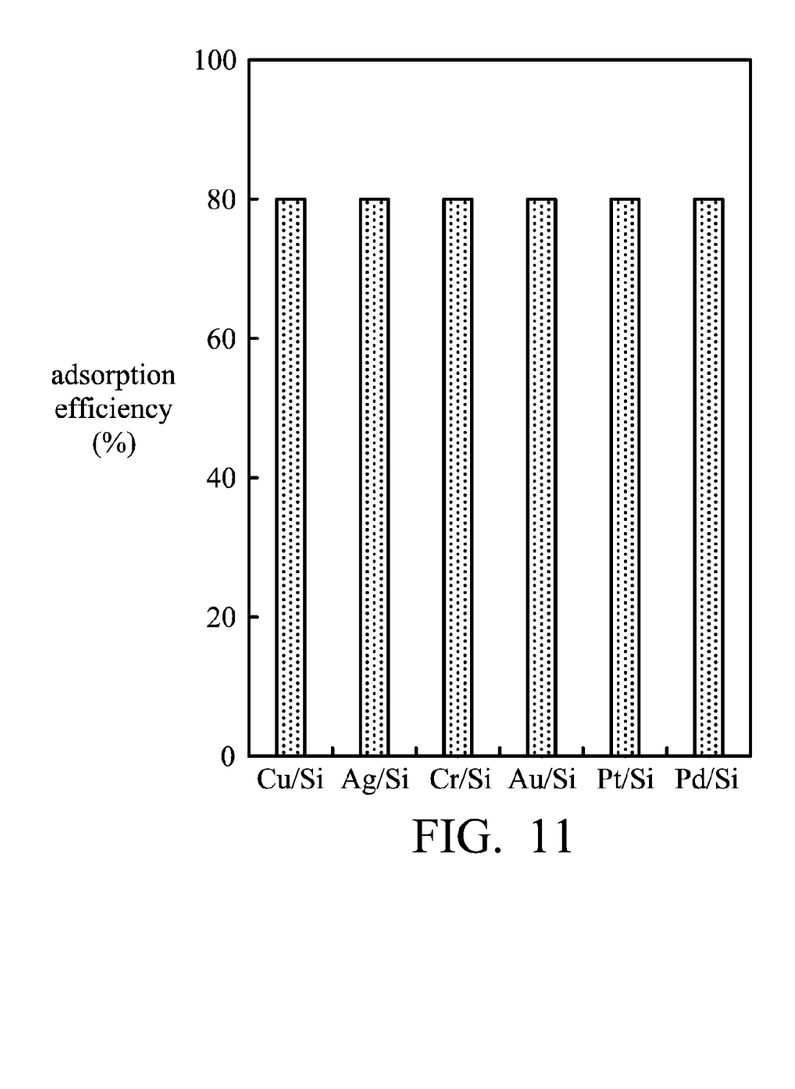
FIG. 11 shows a graph plotting the absorption efficiency of the nanostructure materials of Examples 15-20.

0.1 g of nanostructure materials of Examples 15-20 were respectively disposed in a test chamber 106 of the device shown in FIG. 3 and the absorption efficiency for PH3 of the nanostructure materials was measured. A gas sample (PH$_3$ with a concentration of 500 ppb) 101 and a carrier gas 102 such as nitrogen or noble gases were respectively passed through different mass flow controllers 103, and 104 and mixed together. Valves 105 and 107 were used to control the mixed gas introduced to the test chamber 106 with the nanostructure material therein or introduced to the gas sensor 108 directly for measuring the content of PH$_3$. The nanostructure material was disposed in the test chamber 106 and a carrier platform of the test chamber 106 was covered with the nanostructure material. When the mixed gas was introduced into the chamber, the mixed gas was forced to completely pass thorough the nanostructure material. After adsorption, the remaining gas was measured by the gas sensor 108. The adsorption efficiency of the nanostructure materials of Example 15-20 were measured and the results are shown in FIG. 11. Accordingly, the nanostructure materials with Cu, Cr, Ag, Au, Pt, or Pb oxide had high adsorption efficiency, exceeding the detection limit of 80%.

Accordingly, the invention provides a novel nanostructure material with metallic oxide for detecting phosphorus-containing compounds. Since the nanostructure material with metallic oxide has a mesoporous structure, the nanostructure material with metallic oxide has increased surface area for adsorption of phosphorus-containing compounds, resulting in high detection sensitivity. Further, a detector employing the nanostructure material of the invention can be connected to an FT-IR system to form a real-time gas detector.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A nanostructure material with metallic oxide, comprising a product fabricated by the following steps:
   mixing a silicon oxide or titanium oxide with a surfactant to obtain a first mixture, and subjecting the first mixture to a condensation reaction at a first pH value to obtain a mesoporous silicon oxide or titanium oxide;
   mixing a metal or metallic compound and the mesoporous silicon oxide or titanium oxide to obtain a second mixture, and adjusting the second mixture to a second pH value; and
   subjecting the second mixture to a heterogeneous nucleation, preparing a silicon oxide or titanium oxide nanostructure material with metallic oxide located on a surface thereof.

2. The nanostructure material with metallic oxide as claimed in claim 1, before mixing the silicon oxide or titanium oxide with the surfactant, further comprising mixing the silicon oxide or titanium oxide with a base.

3. The nanostructure material with metallic oxide as claimed in claim 1, after performing the heterogeneous nucleation, further comprising performing an annealing process to obtain the silicon oxide or titanium oxide nanostructure material with metallic oxide located on a surface thereof.

4. The nanostructure material with metallic oxide as claimed in claim 1, wherein the surfactant is gelatine or quaternary ammonium salts.

5. The nanostructure material with metallic oxide as claimed in claim 1, wherein the metal comprises Cu, Ag, Cr, Au, Pt, Pd, or combinations thereof.

6. The nanostructure material with metallic oxide as claimed in claim 1, wherein the metallic compound comprises halide of Cu, Ag, Cr, Au, Pt, or Pd, nitrate of Cu, Ag, Cr, Au, Pt, or Pd, phosphate of Cu, Ag, Cr, Au, Pt, or Pd, sulfate of Cu, Ag, Cr, Au, Pt, or Pd, or combinations thereof.

7. The nanostructure material with metallic oxide as claimed in claim 1, wherein, for the nanostructure material with metallic oxide, the weight ratio between the silicon or titanium and metal of the metallic oxide is between 0.99:0.01 to 0.5:0.5.

8. The nanostructure material with metallic oxide as claimed in claim 1, wherein the first pH value is less than 5.

9. The nanostructure material with metallic oxide as claimed in claim 1, wherein the second pH value is between 6-11.

10. The nanostructure material with metallic oxide as claimed in claim 1, wherein the heterogeneous nucleation is performed at 80-140° C.

11. The nanostructure material with metallic oxide as claimed in claim 3, wherein the annealing process has an annealing temperature of more than 300° C.

12. A nanostructure material with metallic oxide, comprising a product fabricated by the following steps:
   subjecting a first mixture, comprising a silicon-containing or titanium-containing compound and a carbon template, to a first annealing process to obtain a powder;
   mixing a metal or metallic compound with the powder to obtain a second mixture; and
   subjecting the second mixture to a second annealing process, to prepare a silicon oxide or titanium oxide nanostructure material with metallic oxide located on a surface thereof,
   wherein, for the nanostructure material with metallic oxide, the weight ratio between the silicon or titanium and metal of the metallic oxide is between 0.99:0.01 to 0.5:0.5.

13. The nanostructure material with metallic oxide as claimed in claim 12, wherein the silicon-containing or titanium-containing compound has a chemical structure represented by $M(OR_4)$, wherein M is silicon or titanium, and R is C1-8 alkyl group.

14. The nanostructure material with metallic oxide as claimed in claim 12, wherein the metal comprises Cu, Ag, Cr, Au, Pt, Pd, or combinations thereof.

15. The nanostructure material with metallic oxide as claimed in claim 12, wherein the metallic compound comprises halide of Cu, Ag, Cr, Au, Pt, or Pd, nitrate of Cu, Ag, Cr, Au, Pt, or Pd, phosphate of Cu, Ag, Cr, Au, Pt, or Pd, sulfate of Cu, Ag, Cr, Au, Pt, or Pd, or combinations thereof.

16. The nanostructure material with metallic oxide as claimed in claim 12, wherein the first annealing process has an annealing temperature of more than 500° C.

17. The nanostructure material with metallic oxide as claimed in claim 12, wherein the second annealing process has an annealing temperature of more than 300° C.

18. A method for detecting phosphorus-containing compounds, comprising:
   providing the nanostructure material with metallic oxide as claimed in claim 1;
   introducing a gas sample to react with the nanostructure material; and
   analyzing results of the reaction.

19. The method of claim 18, wherein the phosphorus-containing compound comprises phosphine, phosphorusic acid, dimethyl methylphosphonate, trimethyl phosphite, trimethyl phosphate, parathion, parathion methyl, or combinations thereof.

20. The method of claim 18, further comprising connecting the nanostructure material with an FT-IR system for real-time detection and analysis.

21. A method for detecting phosphorus-containing compounds, comprising:
   providing the nanostructure material with metallic oxide as claimed in claim 12;
   introducing a gas sample to react with the nanostructure material; and
   analyzing results of the reaction.

22. The method of claim 21, wherein the phosphorus-containing compound comprises phosphine, phosphorusic acid, dimethyl methylphosphonate, trimethyl phosphite, trimethyl phosphate, parathion, parathion methyl, or combinations thereof.

23. The method of claim 21, further comprising connecting the nanostructure material with an FT-IR system for real-time detection and analysis.

* * * * *